United States Patent [19]

Shalon

[11] Patent Number: 5,192,433
[45] Date of Patent: Mar. 9, 1993

[54] SLURRY COMPRESSOR, APPARATUS FOR GUIDING COMPRESSOR, AND METHOD FOR PACKING SLURRY IN COLUMN

[75] Inventor: Yehuda Shalon, St. Louis, Mo.
[73] Assignee: MODcol Corporation, St. Louis, Mo.
[21] Appl. No.: 870,217
[22] Filed: Apr. 17, 1992

Related U.S. Application Data

[63] Continuation of Ser. No. 501,122, Mar. 29, 1990, abandoned.

[51] Int. Cl.⁵ .................................................. B01D 15/08
[52] U.S. Cl. ........................... 210/198.2; 210/656; 55/386; 141/80
[58] Field of Search ................ 210/656, 198.2; 55/67, 55/386; 141/73, 80

[56] References Cited

U.S. PATENT DOCUMENTS

| | | | |
|---|---|---|---|
| 285,290 | 8/1886 | Shalon et al. | D10/81 |
| 2,178,686 | 10/1936 | Georgiev et al. | 220/89 |
| 3,440,864 | 4/1969 | Blume | 210/198.2 |
| 3,487,938 | 1/1970 | Patterson | 210/198.2 |
| 3,810,545 | 5/1974 | Filz | 210/198.2 |
| 3,878,099 | 4/1975 | Ogle | 210/198.2 |
| 3,885,800 | 5/1975 | Sievenpiper | 277/165 |
| 3,904,527 | 9/1975 | Wilhelmson | 210/198.2 |
| 4,027,816 | 6/1977 | Slator | 277/205 |
| 4,033,380 | 7/1977 | Weber | 138/96 R |
| 4,135,742 | 1/1979 | Anderson | 285/165 |
| 4,309,286 | 1/1982 | Lenihan, Jr. et al. | 210/198.2 |
| 4,350,595 | 9/1982 | Gunkel | 210/656 |
| 4,361,482 | 11/1982 | Teetz | 210/198.2 |
| 4,365,671 | 12/1982 | Long | 166/318 |
| 4,390,043 | 6/1983 | Ward | 138/39 |
| 4,451,363 | 5/1984 | Brownlee | 210/198.2 |
| 4,451,364 | 5/1984 | Higgins | 210/198.2 |
| 4,470,910 | 9/1984 | Quemerais et al. | 210/656 |
| 4,549,584 | 10/1985 | Morin et al. | 141/73 |
| 4,578,193 | 3/1986 | Shephard | 210/656 |
| 4,587,014 | 5/1986 | America | 210/198.2 |
| 4,597,866 | 7/1986 | Couillard | 210/198.2 |
| 4,636,315 | 1/1987 | Allen | 210/198.2 |
| 4,675,105 | 6/1987 | Martin et al. | 210/198.2 |
| 4,719,011 | 1/1988 | Shalon et al. | 210/198.2 |
| 4,861,473 | 8/1989 | Shackelford | 210/198.2 |
| 4,882,062 | 11/1989 | Moeller | 210/198.2 |
| 4,891,133 | 1/1990 | Colvin | 210/198.2 |
| 4,974,707 | 12/1990 | Neumann | 137/599 |
| 5,021,162 | 6/1991 | Sakamoto | 210/198.2 |

FOREIGN PATENT DOCUMENTS

| | | | |
|---|---|---|---|
| 049850 | 4/1982 | European Pat. Off. | 210/198.2 |
| 2409935 | 9/1974 | Fed. Rep. of Germany | 210/198.2 |
| 2250556 | 6/1975 | France | 210/198.2 |
| 60-179653 | 9/1985 | Japan | 210/198.2 |

OTHER PUBLICATIONS

98 Chem Abstract, p. 114 98:56123h (1983).
82 Chem Abstract, p. 197 82:60672y (1975).
105 Chem Abstract, p. 107 105:126340r (1986).
84 Chem Abstract, p. 127 84:76231f (1976).
101 Chem Abstract, 101:57133d.
72 Chem Abstract, p. 119 106:215996x (1987).
Martin et al., An Apparatus for Slurry Packing Preparative LC Colums, Jun. 1985, pp. 1-4.
Zinecker, Praparative Flussigkeitschromatographie under Anwendung der Axialen Kompression der Stat. Phase GIT Fachz. Lab 20-Ig. Jul. 1976, pp. 821, 822 and 824.
72 Chem Abstract, p. 121 72:68562 b (1970).

*Primary Examiner*—Ernest G. Therkorn
*Attorney, Agent, or Firm*—Sandler Greenblum & Bernstein

[57] ABSTRACT

A slurry compressor for obtaining a homogeneous, pressurized, packed absorbent bed of slurry in a chromatographic column is provided. The compressor includes a solid first portion and a second portion which is a slightly tapering walled structure integral with the first portion. An annular groove is disposed within the first portion and a resilient O-ring sealing member is disposed within the ring. A split ring backup-spacer element can also be positioned within said groove to provide increased sealing to prevent leakage of the particles beyond the compressor element. An adapter element for enabling the insertion of the compressor into the column without damaging the surface of the O-ring is also disclosed. A handled straight adapter is also provided to enable the column to be supporting during packing and to be stabilized during column disassembly. A method of packing a column which includes shaking the slurry-filled column prior to pressurizing the column is set forth.

10 Claims, 4 Drawing Sheets

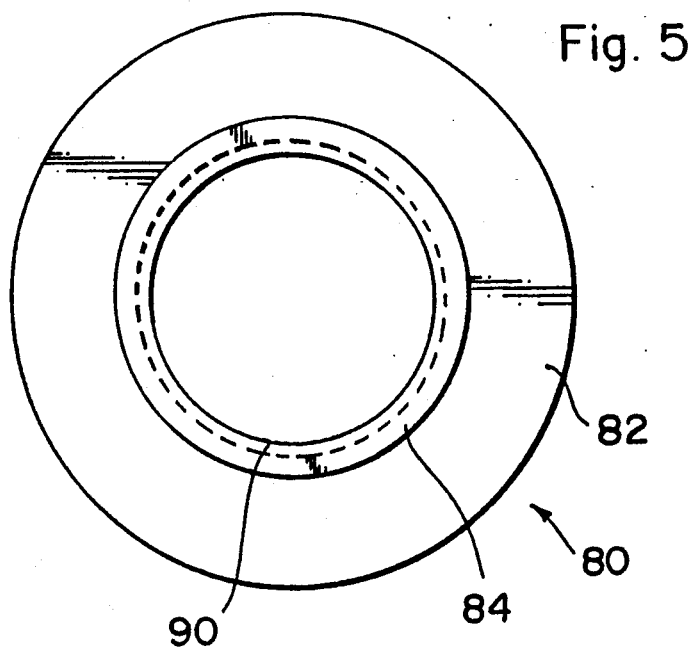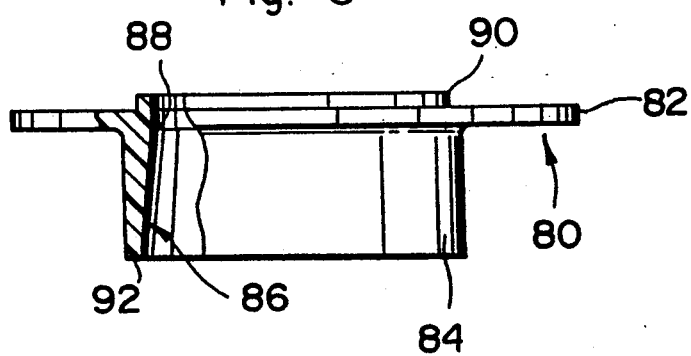

SLURRY COMPRESSOR, APPARATUS FOR GUIDING COMPRESSOR, AND METHOD FOR PACKING SLURRY IN COLUMN

This application is a continuation of application Ser. No. 07/501,122, filed Mar. 29, 1990, now abandoned.

BACKGROUND OF THE INVENTION

1. Technical Field of the Invention

The present invention relates to the field of liquid chromatagraphy. In particular, the present invention is directed to a an improved apparatus for use in obtaining the high and uniformly pressurized slurry beds employed in present liquid chromatography columns, as well as a method for achieving such uniformly packed columns.

2. Description of Background Information

Chromatography is a separation method whereby individual chemical compounds which were originally present in a mixture are resolved from each other by the selective process of distribution between heterogeneous phases. The distribution of chemical species to be separated occurs in a dynamic process between a mobile phase and a stationary phase. The stationary phase, or the column packing material, usually has a relatively large surface area through which the mobile phase is allowed to flow. The chemical nature of the stationary phase exercises the primary control over the separation process. The greater the affinity of a particular chemical compound for the stationary phase, the longer it will be maintained in the system. The mobile phase can be either gas or liquid; correspondingly, the methods are referred to as gas chromatography and liquid chromatography.

Chromatography has been used primarily as a separation and isolation method, and is often intended to separate many mixture components in a single-step procedure. Chromatographic methods can be applied to a very wide concentration range; from commercial scale quantities (gram-kilogram range) all the way to analytical determinations of the order of $10^{-9}$ gram. Chromatographic separations are based upon the physicochemical principals of adsorption and partion, and, conversely, these and related fundamental physicochemical phenomena can be studied by high precision chromatography of model systems.

In liquid chromatography, the mobile phase may be perculated through the column at atmospheric pressure, by means of gravity, or under more contemporary procedures, through the pressure generated by smaller and smaller particles of the packing media. High pressure pumps which can generate up to several thousand atmospheres of inlet pressure are often used.

Thus, high pressure liquid chromatography (HPLC) is a process of separating complex mixtures of chemicals by passing a solution of the chemicals through a stationary column packing material and under a certain degree of pressure. Preparative high pressure liquid chromatography is a process in which one applies a mixture of a compound in solution and in its mobile phase where, by virtue of the selection of the components of the column packing material, the column will retain the various and select components of the mixture for that length of time which causes its select components to be eluted discretely for separate collection as individual components and as purified elements. In preparative HPLC the separation and purification is in larger quantities than in analytical HPLC.

Increasingly, preparative liquid chromatographic separations are being carried out using porous, silica based, or polymeric micro-particulate column packings. These materials offer the advantages of increased resolution and improved overall performance in chromatographic separations.

The field of liquid chromatography has long been utilized in the fields of chemistry, biochemistry and biotechnology. Generally, in practicing the art of chromatography, a slurry is packed within a preparative column under pressure. It has been an ongoing problem in this field to obtain a fine and uniform degree of compactness of the slurry bed within the column as the diameter and length of the preparative column increases in order to obtain the most efficient and effective use of a column during the performance of the chromatographic process. One of the major problems of the prior art packing of liquid chromatography columns has been the formation of bubbles or soft and mushy pockets within the packed bed of the column.

More recently, the field of liquid chromatography has grown to include what is known as high pressure liquid chromatography (HPLC), wherein the columns to be packed are employed in analytical semi-preparative or process columns for use in chromatography. The columns used in chromatographic analysis are generally fabricated of metal, such as stainless steel, and function to separate various chemicals (for analysis or use) that pass through the columns at pressures that range from up to 2000 to 4000 psi. By the use of a liquid chromatography column, the chemicals passed through the absorbent bed are separated into their constituents so that the various desired elements can be obtained, or an analysis of the chemical passing through the column can be performed. A critical feature in ensuring the proper operation of such columns relates to the degree and uniformity of compactness of the packed absorbent bed contained within the column. This slurry packing must be maintained at a very high pressure, and at a uniform density, in order to achieve the most efficient and effective results during the chromatographic procedure.

The present invention relates to the configuration and structure of columns for use in preparative liquid chromatography. The present invention also relates to an apparatus for ensuring the uniformity of slurry and pressure applied to such a column while at the same time minimizing and/or preventing leakage of particles past the pressure applying mechanism. The slurry compressor of the present application facilitates obtaining a homogeneous absorbent packed bed in liquid chromatography columns, thus improving the efficiency of the columns and increasing the accuracy of the results obtained thereby. The particularly designed and styled compressor of the instant application is particularly designed to eliminate the leakage of particles past the compressor while at the same time enabling very high and uniform pressures and densities to be achieved. The present invention also relates to an adapter or tool which facilitates and/or enables insertion of the inventive slurry compressor into the column without damaging the compressor or the sealing members carried thereby. The present invention also relates to a method of mixing the slurry prior to packing to enhance its separating qualities.

The instant slurry compressor is an improvement over the compressor disclosed in U.S. Pat. No.

4,675,105 (MARTIN et al.) entitled "System for Obtaining a Homogeneous Absorbent Bed in a Chromatographic Column".

The present invention also relates to a handled straight adapter for use between two chromatographic columns that facilitates packing of the working column from an attached reservoir column. The instant handled straight adapter is an improvement over the adapter disclosed in U.S. Pat. No. 4,719,011 (SHALON et al.) entitled "High Pressure Liquid Chromatography Columns".

One very successful solution to the problem of achieving high and uniform pressures and densities within liquid chromatography columns is set forth in the above-mentioned MARTIN et al. patent. In that patent, a slurry compressor is disclosed for obtaining a homogeneous absorbent bed in a liquid chromatographic column. The compressor includes a solid, shaped compressor member having external dimensions only very slightly less than the internal dimensions of the column in which the bed of particles being compressed is contained. The compressor includes an innermost portion which, in use, is in contact with the particles within the column and an outermost portion integrally connected to the innermost portion. The innermost portion is a solid segment while the outermost portion is formed with a hollowed interior forming a walled structure extending rearwardly from the solid portion. The walled structure of the outermost portion is shaped to flare slightly outwardly from the inner portion in order to tightly and sealingly contact the inner wall surface of the associated reservoir column. Thus, the flared wall portion acts as a seal, preventing the slurry from leaking past the compressor element.

While the above mentioned prior art slurry compressor has functioned well, a need nevertheless exists for an improved sealing mechanism for preventing leakage of slurry past the compressor, particularly at the very high pressures used in modern chromatographic systems. The present invention solves this problem by providing a slurry compressor designed in such a manner so as to prevent leaks of slurry therepast within the column.

Also provided in the present invention is a tool and adaptor element that cooperates with the slurry compressor and with the column for enabling the slurry compressor to be quickly and efficiently inserted into the liquid chromatographic column without damaging any portion thereof.

The present invention thus relates to an improved slurry compressor having an improved resilient sealing means, to an adaptor tool for inserting the compressor into the chromatographic column without damaging any portion thereof, to a method of mixing the slurry prior to compression thereof, as well as to an adaptor element with outwardly extending handles.

The efficiency of the column used in liquid chromatography is very strongly influenced by features such as the length and/or width of the column. Thus, to be able to separate a large variety of chemical compounds it has in the past been necessary to maintain in storage, have available or purchase a large variety of columns of various lengths and/or widths. This of course has been extremely cumbersome, not to mention expensive and inefficient. A very successful solution to the problem of the non-adaptivity of the various columns to a wide variety of chemical compounds was proposed by the aforementioned SHALON et al. patent. Therein, a modular chromatographic column was proposed. According to the disclosure of the above patent, columns of varying length and width can be coupled together through the use of a variety of adapters. The system disclosed is quite easy to assemble because all of the components thereof are modular and are very convenient to handle. Thus, a large stock of different lengths and widths of columns is no longer needed. Practice of the art of liquid chromatography has been simplified and thus greatly enhanced through the use of a relatively limited number of modular components.

The above-mentioned modular liquid chromatography system has been quite successful in providing a wide range of column widths and lengths by virtue of the use of various types of adapters, such as straight adapters for connecting columns of equal diameter and conical or tapered adapters for connecting columns having different diameters. However, in the use of these adapters a problem in removing the adapter from the column itself occasionally arose. The present invention solves this problem by providing an adapter having handles integrally attached thereto to facilitate removal of the adapter from the column. After a bed has been pressurized and packed within a column and an associated reservoir column, and the reservoir column is removed prior to the use of the packed working column, the bed has tended to expand upwardly and outwardly away from the working column. As the pressurized bed expands upwardly, as a result of the removal of pressure therefrom, it can become damaged, e.g., by breakage. The present invention solves this problem by providing an adapter having handles attached integrally thereto to facilitate restraining the upward expansion of the pressurized slurry bed from the working column. This permits removal of the reservoir column from the working column and removal, as by a wire knife or other means, of the extra packing media from the working column as it expands therefrom. The use of the instant handled straight adapter which is used to connect both columns prevents damage to the prepared packed bed within the working column.

The present invention also relates to an improved straight adapter for coupling two column portions together. The improved adapter of the present invention is provided with handles so that during use (i.e., filling and packing of the column) the column can be stabilized by being attached to a support structure via the handles attached to the adapter, and upon disassembly of the columns, because of the handles provided on the adapter, the prepared packed column bed is not damaged.

Since the filling, assembly, and pressurization (packing) of the column takes some period of time, the filling material (slurry mixture) often tends to undesirably settle out during the filling process. According to a further feature of the present invention, a method for filling and preparing chromatographic columns is set forth that eliminates such problems and enables the columns to be filled in such a manner that the contents of the slurry bed therein remain uniform. This has made the slurry packed columns much more efficient and effective in being utilized for preparatory chromatography.

The double sealed slurry compressor with the flared end up is inserted on the top of the reservoir column with the aid of the compressor adapter. Once the compressor is in place the adapter is removed form the reservoir column. The top of the reservoir column is now sealed with a large O-ring and an end plate. The end plate is mounted securely with bolts and nuts. This endplate will later be connected to the packing instrument.

According to a most significant feature of the present invention, after the working and reservoir columns have been mounted together with the inventive straight handled adapter mounted therebetween, the mixed slurry is then poured into the assembled columns. The assembly is not filled totally, thus a substantial amount is left empty, which will create an air bubble in the assembly. The working column is now sealed with a large and small O-ring, a bed support frit, a disperser frit, and an end plate and tightened with bolts and nuts. The assembled columns are now sealed and shaken or mixed so that the contents (i.e., the slurry mixture) are mixed so that the air bubbles contained within the column will serve as a mixture device to maintain the homogeneous nature of the slurry and prevent settling out of the slurry components prior to the application of pressure to the slurry filled assembly. Immediately thereafter, the slurry can be pressurized to a uniform and high pressure and density by applying pressure to the instant improved double sealed slurry compressor, which is positioned on top of the reservoir column which is attached to the packing instrument. After the system has been pressurized and allowed to equilibrate for a period of time, the procedure of removing the reservoir column from the working column can be performed only after the pressure is released. First, most of the nuts and bolts connecting the straight adapter and reservoir column to the working column are removed, and the remaining ones are loosened, so that a cutting wire can be inserted to cut the slurry between the columns with a cutting wire. The reservoir column is then very carefully removed while a stainless steel plate is placed on top of the packing media within the handled straight adapter (not yet removed from the working column). The plate and handled straight adapter are then held in place securely while the attaching means, that attach the straight adapter to the support structure of the column, are loosened. The straight adapter can then be removed making sure not to destroy the integrity of the packed bed. After this, the working column is sealed by attaching thereto the end plate, various frits, sealing O-rings and other mechanisms by means of nuts and bolts, the nuts and bolts are tightened, and the packed column is ready for use.

SUMMARY OF THE INVENTION

The invention involves a slurry compressor for use in a chromatographic column adapted to contain a bed of particles comprising a slurry, the compressor being a shaped member having an inner portion and an outer portion. The inner portion is a solid segment that includes a generally planar surface which is adapted to contact the slurry, while the outer portion is a hollowed interior defined by a walled structure extending from the solid segment forming the inner portion. The inner portion includes an annular groove positioned intermediate the generally planar surface and the outer portion and the groove comprises means for receiving a resilient means adapted to seal an interface of a column and the compressor.

The compressor further including resilient means, for sealing that is positioned within the groove, and comprises a resilient O-ring. The groove further includes means for receiving at least one backup spacer member. The walled structure includes walls which flare slightly outwardly from the inner portion. The slurry compressor is formed of a polymer and the inner and outer portions of the slurry compressor are integrally connected. The resilient sealing means is a resilient O-ring and includes at least one backup spacer element positioned within the groove. The backup spacer element is positioned between the O-ring and the generally planar surface and comprises a split ring of glass loaded polymer. Two backup spacer elements can be positioned in the groove with the O-ring positioned between the spacer elements. The O-ring, spacer element and the wall structure each comprise means for sealing an annular space between the column and the compressor.

The invention also relates to an adapter comprising means for engaging the column opening and means for receiving and guiding the compressor into the column opening.

The invention relates to a receiving and guiding means that comprises a tapering funnel member and an engaging means that comprises a support element engaging the column opening with a first flange engaging a top wall surface of the column opening and a second flange engaging a side wall surface of the column opening. The receiving and guiding means comprises a hollow tapering funnel member and the engaging means comprises a flanged hollow member.

The invention also includes a liquid chromatography column in combination with the adapter apparatus which includes a hollow tapering funnel member and a flanged hollow member.

The invention further sets forth an apparatus for obtaining a slurry comprising a homogeneous absorbent bed of particles in a chromatographic column under pressure. The apparatus includes a slurry compressor including a first portion comprising a slurry contacting face and a second portion comprising a pressure receiving surface with a resilient member positioned about the first portion so as to comprise resilient means for sealing the particle bed and the second portion comprising second means for sealing the particle bed. The second sealing means comprises a walled structure flaring outwardly from the first portion and the resilient means comprises a resilient O-ring positioned within an annular groove of the first portion. The resilient means comprises a resilient O-ring and a backup spacer element positioned within an annular groove of the first portion. The backup spacer element comprises a flat, annular split-ring element.

Further, the invention relates to an adapter element for use between two terminally flanged columns of a chromatography assembly with the columns adapted to be assembled with the adapter element positioned between them. The adapter element is an annular member having an exterior periphery and an internal aperture, the internal aperture defined by a diameter which is generally similar to the internal diameter of the column and means for stabilizing the adapter during disassembly of the columns and attached to the exterior periphery of the annular member.

The stabilizing means comprises a plurality of handles extending outwardly from the annular member. The stabilizing means further comprises means for securing the adapter to a support structure. The handles comprise means for preventing a compressed slurry within a chromatographic column from expanding out of the column. The handles also comprise means for attaching the assembly to a stabilizing support structure. The handles can include a reinforcing rib and clamping means can be attached to the handles.

The invention further involves a method of packing a chromatographic column with a slurry. The method comprising the steps of inserting a slurry compressor element into a reservoir column, assembling the reservoir column to a column to be packed, pouring a slurry into the assembled columns, shaking the assembled columns with the slurry therein and uniformly compressing the slurry within the assembled columns by applying pressure to the slurry in the working column via the compressor element positioned within the reservoir column. The method further includes the step of disassembling the reservoir column from the packed column containing the slurry and the step of inserting a slurry compressor into a reservoir column includes installing an O-ring and a backup member in a groove of the slurry compressor element. The step of assembling the reservoir column and the column to be packed includes positioning a handled straight adapter between the columns.

According to a further feature, the step of assembling the reservoir column to the column to be packed further includes attaching the handles of the handled straight adapter to a support surface. The step of disassembling the reservoir from the packed column includes loosening the reservoir column assembly bolts and cutting through the packed slurry. The step of disassembling the reservoir column from the packed column includes the step of removing the handled adapter from the opening of the packed column. The step of disassembling the reservoir column from the packed column includes cutting the packed slurry bed level with the column opening, after removal of the straight handled adapter.

BRIEF DESCRIPTION OF THE DRAWINGS

The invention is further explained in the detailed description which follows, with reference to the drawings, by way of non-limiting examples of the various embodiments of the invention, in which like reference numerals represents similar parts throughout the several views, and wherein:

FIG. 5 is plan view of one end of the compressor adapter or tool of the present invention that is used to insert the slurry compressor into the reservoir column;

FIG. 6 is a cutaway sectional—and side view of the compressor adapter of FIG. 5;

DESCRIPTION OF THE PREFERRED EMBODIMENT OF THE INVENTION

Figure 1:
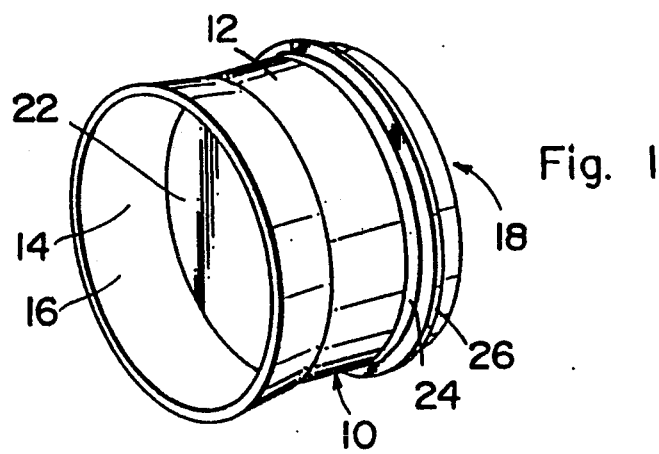
FIG. 1 is a perspective view of the slurry compressor of this invention.

With reference to the drawings and in particular reference to FIG. 1 there is illustrated, in perspective, a slurry compressor 10. The compressor comprises a generally cylindrically shaped element 10 having a first portion, referenced as the inner portion, and terminating in a planar front surface 18, and a second outer or rear portion which is opposite to and integrally joined with the inner portion. The inner portion is a solid cylindrical member 12, defined by a first planar surface 18, which, in use, is adapted to be driven by hydraulic pressure or other means against a slurry which usually comprises a bed of silica particles. The opposite end surface 22 of the inner portion 12 of the compressor 10 is seen to be the bottom surface of a generally hollow walled structure which is fabricated integrally with the inner portion. Thus, the outer or rear portion of the compressor comprises the circumferentially arranged, generally frustoconical flexible wall 14, and the surface 22, which together define a hollow recess 16 in the back end of the compressor element. The back end of the compressor element is the end to which a hydraulic (or other) force is applied to compress the slurry which is in contact with the surface 18 of the inner portion of the compressor element. The size of the compressor element at the inner portion and at the surface 18 is selected to be very slightly less than the inner diameter of the chromatographic column, (e.g., a reservoir chromatographic column) within which it is to be employed. As seen in the drawings, and most particularly in FIG. 4, the circumferential wall 14 flares slightly outwardly from the body of the compressor in a radial manner so as to provide a tight seal against the inner wall surface of the column. The use of tapered walls having a dimension such as to abut tightly, by virtue of their resilience, against the inner surface of the column, is designed to prevent the leakage of slurry past the compressor element. Further disclosure of the structure and use of a predecessor slurry compressor element is contained in the above-referenced patent to Martin et al. (U.S. Pat. No. 4,675,105), the entire disclosure of which is expressly incorporated herein by reference.

In order to further assist in sealing the compressor within the reservoir column and to prevent leakage of slurry particles therepast, the compressor element 10 is provided with an annular, generally rectangular in cross-section groove 22, adjacent surface 18. As shown most clearly in FIG. 4 of the drawings, the annular groove 22 is inscribed in the circumferential wall of the compressor element inner portion and is generally parallel to the bottom surface thereof. A flexible O-ring sealing member 26 can be disposed within the groove 22 to serve to resiliently abut against the walls of the chromatographic column 60, and to act as a seal to prevent any of the slurry from leaking past the compressor element 10.

Figure 4:
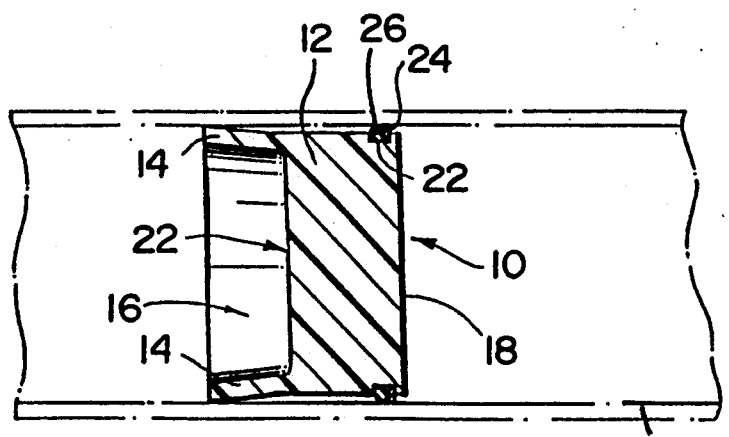
FIG. 4 is a sectional view of the compressor of the present invention, taken along the section line 4—4 of FIG. 2, and showing in phantom lines schematically a part of a chromatographic column within which the slurry compressor is utilized.

A split ring spacer or back-up element 24 formed of a plastic material and designed to support, position and backup the flexible O-ring 26, is also positioned within the groove 22. In practice, either one or two split ring spacer elements 24 can be provided. If two such rings are provided, one would be positioned on either side of the flexible O-ring within the groove 22. If only one split ring spacer element 24 is provided, it should be located on that side of the flexible O-ring opposite to which a (hydraulic) pressure is applied. Thus, if only one split ring spacer element is provided, it would be located relative to the O-ring and the bottom surface 18 as shown in the sectional view of the FIG. 4. While only one split ring spacer/back-up element is shown in FIG. 4, it is explicitly within the scope and contemplation of the invention that two (or more, for that matter) back-up spacer rings 24 can be utilized herein, in which case one would be positioned on either side of the resilient O-ring 26.

The split ring backup spacer elements 24 are fabricated of a glass loaded polymer material so as to provide additional structural rigidity and support for the resilient O-ring 26, which is formed, e.g., of a suitable elastomer. The outer diameters of the O-ring 26 and the split ring backup spacer 24 are substantially the same. Both of these elements provide additional sealing for the slurry particles contained in the liquid chromatography column 60. These sealing mechanisms provided by the ring 26 and spacer element 24 are in addition to the sealing action provided by the resilient nature of the tapered walls 14 of the slurry compressor element itself.

When two backup spacer rings 24 are provided, they provide additional backup for the resilient O-ring 26, giving it more body and rigidity and enabling a better pressure seal to be maintained against the column walls. In practice it has been found that the plural cumulative pressure sealing mechanisms provided by the O-ring 26, split ring 24 and tapered walls 14 contributes to an exceptionally efficient and well functioning liquid chromatography column pressurizing and packing mechanism, which is much improved over that of the prior art.

In order for the compressor and the improved seal mechanism thereof to perform their respective functions properly, the O-ring 26, seated within the groove 22 must seal perfectly with the inner walls of the chromatographic reservoir column 60. Chromatographic columns are generally made of stainless steel and the interior surfaces of these columns are finished to a very high degree of smoothness. However, at the mouth of the column where the compressor element of the invention is inserted, the column wall surface might be marred by imperfections. The compressor body itself is very slightly smaller that the column into which it is to be inserted; however, the O-ring, in order to function properly, must be slightly larger then the column, and must as a result, be inserted into the column with a great deal of pressure. Accordingly, it can happen, when inserting the slurry compressor element, assembled with the O-ring and spacer, into the mouth of a column, that the various nicks, burrs and imperfections at the mouth of the column cause the O-ring to become damaged. In other words, scratches or nicks can occur in the surface of the O-ring. As can be understood, this causes the O-ring to lose a great deal of its efficiency in sealing the slurry contained under the compressor, especially when the compressor is pressed against the slurry under the extremely high hydraulic pressures utilized in contemporary chromatography columns and applied to the outer portion of the compressor element. In order to avoid these problems, the adapter member illustrated in FIGS. 5 and 6 has been developed.

Figure 2:
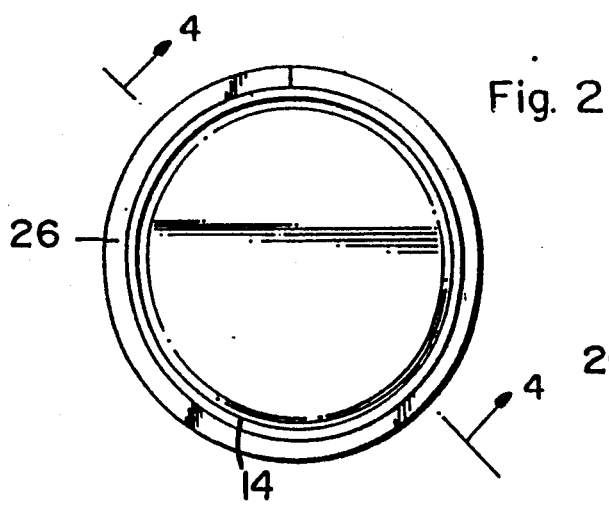
FIG. 2 is an end view of the slurry compressor of FIG. 1, directed at the outer or rear portion thereof.
Figure 3:
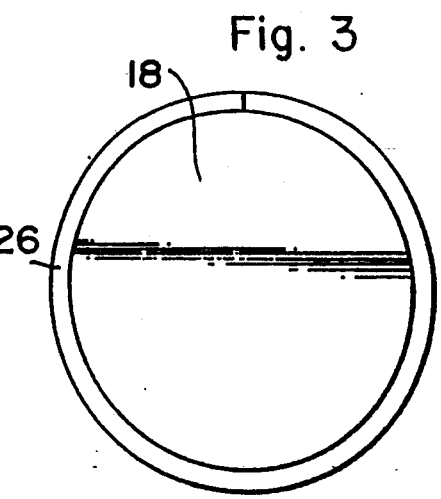
FIG. 3 is an end view of the slurry compressor of FIG. 1, directed at the inner or front portion thereof.

The adapter member shown in end view in FIG. 5, and in side view with a partial section in FIG. 6, essentially acts as a funnel to assist and facilitate the insertion of the compressor element shown in FIGS. 1-3 into the chromatographic reservoir column, as shown in FIG. 4, without causing any damage to the resilient surface of the O-ring thereof.

As shown in FIGS. 5 and 6, the adapter, generally designated as 80, is formed of stainless steel or other similar durable and smooth material. The top portion (as used) of the adapter member is a generally hollow cylindrical component 84 having frustoconical inner walls with a slight interior taper, as shown at 86, and an axially extended, generally annular flange member 82 connected to the walls 84. Opposite the walls 84, on the other side of the flange member 82, a second, relatively short, upstanding cylindrical member 90 is provided. This member 90 is also hollow and acts as a continuation of the funnel shaped component 84, as shown in the partial sectional view of FIG. 6. As noted above, and as seen in the partial section view of FIG. 6, the walls 84 of the interior of the cylinder taper inwardly from a somewhat wider opening at the mouth outer portion 92, to a slightly narrower portion extending inwardly from the inner surface of the adapter. Beyond the tapered portion 86, the adapter has a rounded transition portion 88. The wall then extends into the uniform dimensioned entrance portion which comprises the interior of the upstanding member 90.

Figure 10:
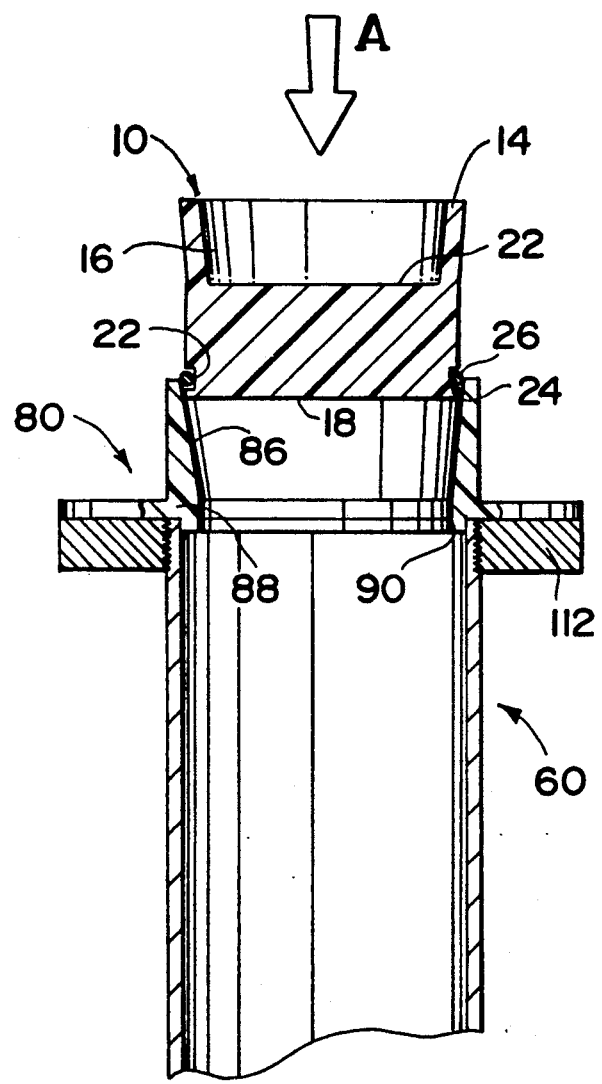
FIG. 10 is a sectional view of the compressor adapter mounted to a column with a slurry compressor being inserted to the column via the adapter.

In operation, and as shown in FIG. 10, the member 90 and the supporting flange 82 are placed over the inlet portion of a stainless steel chromatographic reservoir column. The compressor, with the split ring spacer back-up member 24 and resilient O-ring 26 positioned within the groove 22, are then inserted into the outer portion or mouth of the funnel 86. By virtue of the guiding and slowly tapering shape of the funnel section 84, 86, the compressor can be safely and without damage inserted into the column 60 to attain the position of FIG. 4. The degree of taper of the walls 86 is not critical, but should be fairly slight and should also be adequate to enable the compressor to be pushed therethrough and into the column inlet. As can be readily understood, the shape and structure of the tool/adapter 80 is such as to prevent any damage occurring to the resilient ring of the compressor element as it is being inserted into the column. FIG. 10 shows the adapter 80 positioned with the wide portion of the funnel section 84, 86 facing upwardly over the inlet mouth (or top) of a reservoir column 60 having a flange 112 positioned there at. Also shown is with a slurry compressor 10 (with the resilient O-ring 26 and split ring backup spacer member 24 positioned in the groove 22) positioned with the flared portion facing upwardly, at the inlet of the adapter. The adapter flange 82 is positioned in overlying relation to the column flange 112. By the application of pressure from a suitable source in the direction indicated by the arrow A, the slurry compressor can be fully inserted into the reservoir column and the adapter 80 quickly removed.

One of the principal advantages of the chromatography system disclosed in SHALON et al. (U.S. Pat. No. 4,719,011), the entire disclosure of which is expressly incorporated herein by reference in its entirety, is that the modular nature of the system disclosed enables great versatility; thus the components can be quickly assembled into various desired configurations. This eliminates the need for large stocks of seldom used components to be maintained. An essential component of any modular system is that the individual components thereof are easily connectable. In the above modular chromatographic system, this connectability is provided through the use of flanges at the end portions of each of the columns. Also, between connected columns adapters are utilized. The above-mentioned patent discloses and describes various forms of adapters including a straight adapter, a frit adapter and a tapered and/or conical adapter. The present invention also involves an improved handled straight adapter for use in packing chromatographic columns of the type disclosed and discussed in the above-mentioned SHALON et al. patent. In particular, an improved handled straight adapter designed to enable efficient packing of chromatographic columns from attached reservoir columns without damaging the compressed slurry bed contained therein, is provided by the present invention.

Figure 7:
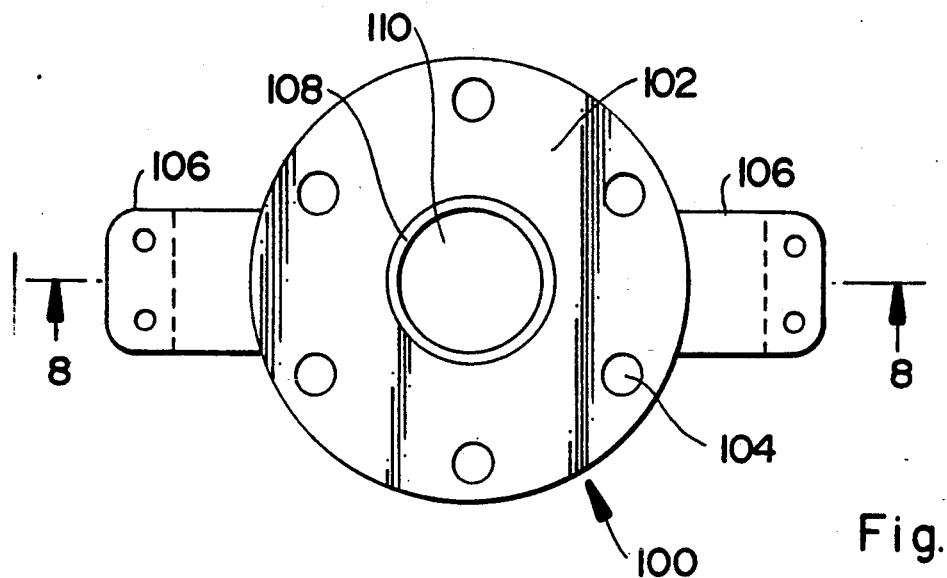
FIG. 7 is a plan view of one end of the handled straight adapter/connector of the present invention.
Figure 8:
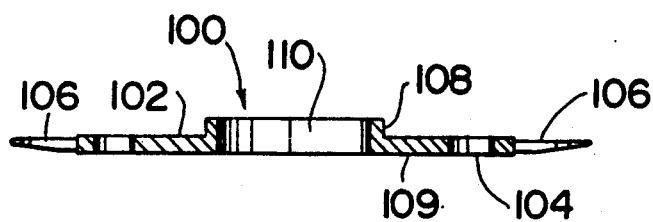
FIG. 8 is a side sectional view of the handled straight adapter/connector of FIG. 7, taken along section lines 8—8 therein.
Figure 9:
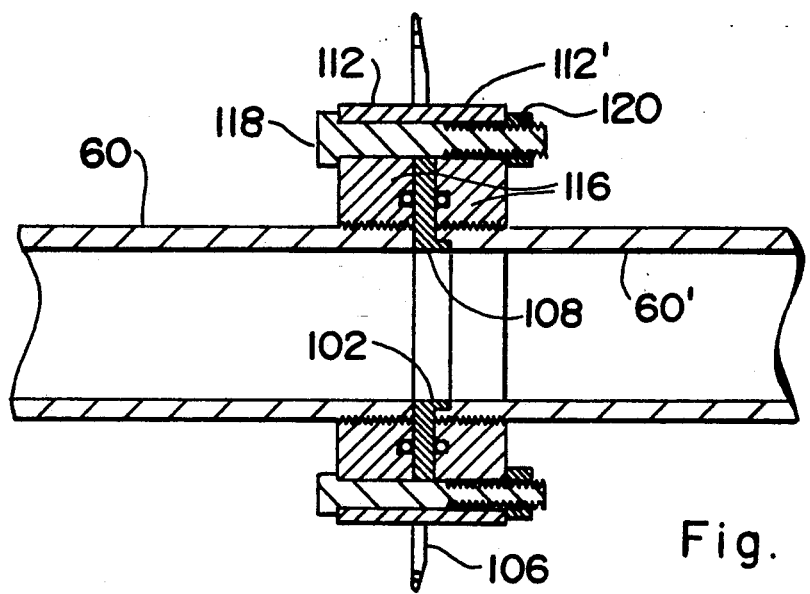
FIG. 9 is a sectional view of the handled adapter/connector of FIGS. 7 and 8, installed between two chromatographic columns according to one feature of the present invention.

The improved straight adapter of the invention is illustrated in FIGS. 7-9. With particular reference to FIG. 7, an end view of the adapter 100 is shown. The adapter comprises an annular section 102 provided with a plurality of bolt holes 104 spaced thereabout. These holes, as can be seen in FIG. 9, are engaged by bolts 118 which also pass through the opposed flanges 112, 112' of the working column to be packed 60', and the reservoir column 60, which are to be joined through the intermediary of the herein described adapter 100. Adjacent to the interior annular aperture 110, there is provided, on one side, an upstanding flange 108 as the interior boundary surface of the straight adapter. As can be seen in reference to FIG. 9, this upstanding flange 108 is seated within a correspondingly provided annular groove in the end face of the column 60' to be packed. The use of this annular flange 108 provides the interior surface of the joined columns with an uninterrupted smooth surface. The other side of the straight adapter is provided with a flat surface 109. At opposite ends of the external surface of the adapter 102, outwardly extending, elongated generally flat handles 106 are provided. These handles, attached to the straight adapter, assist in the stabilization of the connected reservoir and packing column during the assembly thereof. The use of these handles and the attachment of these handles to any convenient support structure (by conventional attaching elements not shown herein) also facilitates the shaking and agitation of the connected columns to ensure that the homogeneous nature of the slurry is maintained during the filling process before packing the slurry. The flat surface 109 of the straight adapter enables straight and even cutting of the packing media with a wide knife or a similar tool across the inner diameter above the packed column. Moreover, the straight adapter with handles also assists in the removal of the adapter from the columns after the slurry has already been compressed within the connected reservoir and working columns. The use of the handled straight adapter and, in particular, the use thereof in the disassembly of the reservoir column from the packed working column, enables the compressed slurry to be maintained in an undisturbed condition. This enables slurries of exceptional uniformity to be produced. Such columns are extremely desirable in the chromatographic art and are essential to the achievement of accurate results in this field.

The structure of the handles of the straight adapter can be seen with reference most particularly to FIGS. 7 and 8. As seen in these Figures, the handles are provided with a somewhat tapered cross-sectional area, and the central portion thereof can be provided with a rib (not shown) so as to provide additional strength to the handles. While this ribbed structure contributes to the strength of the handles, it is not an essential part of the handle structure per se. In particular, and if necessary, any other conventional reinforcing mechanism to ensure that the handles have the adequate strength for the uses for which they are designed can also be utilized therein. Since one of the functions of the handles when used between attached reservoir and packing columns is to be attached to an appropriate support structure, various attachment means can be included in the structure of the handles. The straight handled adapter shown in the drawings is noted to show a plurality of apertures through the outwardly extending portions thereof. The locations of these apertures are merely exemplary. The positioning of the apertures and/or of additional structure that can be utilized to provide a support for appropriate securing mechanisms that could be attached to the adapter, and the columns to which it is assembled, to in turn enable the adapter to be supported, can be modified as needed. On the other hand, these apertures can readily be eliminated, and other conventional means can be used for attaching the handled adapter to an appropriately located support structure.

FIG. 9 shows the improved handled straight adapter joining a reservoir column 60 to a chromatographic column 60' to be packed with a slurry bed. Each column is provided with a flange member 112, 112' attached to the outer surface of the end portion thereof. Each of the flange members has an annular recess in an end surface thereof for receiving therein a sealing O-ring 116. As can be seen in the figure, the O-rings 116 abut opposite sides of the straight adapter 102, and act as seals between these components.

In operation, the two flanges are assembled face-to-face, and nut and bolt assemblies 118 and 120 are inserted into the appropriate holes positioned about the periphery of the annular flanges in an array corresponding to the holes 104 illustrated in FIG. 7 for the straight adapter. As all of these holes are aligned, the bolts 118 and mating nuts 120 can be inserted and tightened down to form a single unitary chromatographic column. In FIG. 9, the flange 108 of the straight adapter, in its use orientation, can be clearly seen. As can be further observed from FIG. 9, the handles of the straight adapter extend outwardly beyond the flanges 112 and are visible when the mechanism is in use. The handles enable the joined columns to be secured to an appropriately positioned support structure (not shown). The support structure utilized can be, e.g., a column support stand specifically designed to support a column or columns or any other support structure that is positioned with respect to the joined columns so as to enable the columns to be secured thereto.

After the combined columns have been secured, they can be positioned in such a way that the slurry which is going to form the compressed bed can be poured into the combined columns. At this point in the process, another significant feature of the present invention is utilized. At this point, the slurry in the column is mixed by tilting and/or shaking the assembled columns in any convenient and conventional manner. Any form of mechanical agitating or mixing device can be used, or depending on the size of the columns they can be mixed by merely being shaken up and down or in any other fashion to enable the air bubbles therein to mix and maintain the homogeneous nature of the slurry within the column. Substantially enhanced results are obtained by utilizing a column wherein the slurry therein has been mixed by mechanical agitation or by any other mechanism so as to ensure that the homogeneous nature of the slurry contained within the column is maintained. After the slurry is mixed and the pressure supplying mechanism is attached to the column by means of provided line fittings, the slurry can then be pressurized to form a solid bed. Compression of the slurry bed or packing of the column under pressure is performed utilizing the improved slurry compressor disclosed in this application. The double sealing mechanism of the above disclosed slurry compressor is very advantageous in preventing leakage of the slurry past the compressor element during the packing of the column. After the appropriate pressure had been applied to the slurry within the column for a predetermined period of time depending on the pressure desired, the system and the packed column is allowed to equilibrate for a period of time. At this time it is essential to remove the reservoir column from the packed column and to properly connect the packed column, without in any way disturbing or destroying the uniformity of the packed bed therein, to the appropriate instruments and supply lines as dictated by the ultimate intended use of the packed column. As will hereinafter described, the straight handled adapter of the present invention plays a major role in ensuring the disassembly of the reservoir column from the packed column without disturbing the condition of the packed slurry bed within the packed column.

A major function of the enhanced handled straight adapter is to assist in the stabilizing of the silica slurry in the column during the separation of the reservoir column from the working column after it has been packed. Prior to the packing of the working column, the working column is attached, via the flanges 112, 112', to a reservoir column. The packing media is inserted through the reservoir column and is compressed downwardly into the working column by use of the slurry compressor. After the working column is fully loaded with compressed silica, the reservoir column is removed. Because, during the packing process, the packing media slurry is compressed under great pressure, upon removal of the reservoir column, the packing media naturally tends to expand outwardly from the mouth of the packed column. Should the expanded packing media, because of its own instability, break off and break with it some of the packing within the working column, the efficiency of the packed working column would be severely impacted. Thus, according to the present invention, by the use of the straight adapter with the handles as shown herein, upon removal of the reservoir column, the expanding packing media out of the working column can first be shaved off by the use of a straight edge wire or similar implement. Thereafter, by the use of any circular plate sized to fit into the central aperture of the handled adapter, downward pressure can be exerted on the slurry within the working column to prevent it from expanding out of the column and, by use of the handles provided, the adapter can then be removed; thus avoiding the possibility of the packing media expanding out of the column and breaking off and deteriorating the usability of the slurry packed column. Moreover, during use (i.e., assembly and packing), the handles 106 are generally secured, as by rings or clamps, to any convenient support structure so as to provide further stability to the column itself.

The disassembly of the reservoir column from the packed column according to the invention is performed in the following manner. First, after the pressure is released, the majority of the nuts and bolts connecting the reservoir column to the working column, i.e., packed column, are removed. Two opposite bolts are allowed to remain and these are loosened so that a cutting wire or other implement, as noted above, can be inserted, and the slurry bed within the still-joined columns can be cut through from one end to the other. Thereafter, the last two nuts and bolts can be removed, after which the reservoir column can (and should) be removed from the column containing the packed slurry bed. At this point, the straight handled adapter is still positioned on top of the packed slurry within the column that has been packed under pressure. A plate is then placed on top of the slurry, within the central aperture of the handled adapter. The plate and straight adapter are then held securely by applying pressure downwardly to prevent the adapter and plate from lifting up due to the expansion of the compressed slurry thereunder. The straight adapter can then be detached from whatever support structure it was attached to prior to packing of the slurry within the chromatographic working column; and, thereafter, the straight adapter and plate can be carefully removed, making certain not to destroy or in any way mar the finish of the packed bed. A straight edge sharp knife or other appropriate implement can then be used to cut the packed bed flat at the height of the flange in the mouth of the packed column. At this point, the various frits and sealing O-rings can be assembled into the flange grooves and an appropriate end plate can be installed and bolted to the flange of the column. After this operation is completed, the packed column is ready for use.

Thus, the handled straight adapter of the present invention enables the columns to be disassembled without damaging the packed slurry therein and thus contributes to the efficient packing of columns. It also enables the columns to be agitated and mixed to enable the slurry within the columns as it is being inserted therein to be maintained as a homogeneous mixture.

As mentioned above, the chromatographic columns for which the invention is set forth herein are generally formed of a stainless steel. The compressor element which is the subject of the instant invention can be fabricated, e.g., of a technical grade TFE. The O-ring can be formed, e.g., of a florez material. The split ring spacer backup member can be formed, e.g., of a glass loaded TFE material. The adapter 80 and the straight adapter 102 can each be fabricated, e.g., of stainless steel or aluminum. The above mentioned material of which the various components of the present invention can be fabricated are not intended to be limiting in any manner. Various other, materials with satisfactory properties can be utilized as an alternative herein. The above materials are merely included for the illustrative purposes of showing a particular preferred material of which the components of the present invention can be fabricated. Different materials can obviously be utilized and still remain within the scope of the present invention.

Although the invention has been described herein with reference to particular means, materials and embodiments, it is understood that the invention is not to be limited to the particulars disclosed herein, and that the invention extends to all equivalents within the scope of the appended claims.

I claim:

1. A slurry compressor for use in packing a chromatographic column adapted to contain a bed of particles comprising a slurry, said compressor comprising a shaped member having an inner portion and an outer portion, said inner portion comprising a solid segment that includes a generally planar surface that is adapted to contact slurry, said outer portion comprising a hollowed interior defined by a wall structure sized for contacting a chromatographic column wall and extending from the solid segment forming the inner portion, said inner portion including an annular groove positioned intermediate said generally planar surface and said outer portion, said groove comprising means for receiving resilient means adapted to seal an inner face of a column wall and said compressor when said compressor is in a chromatography column, and further including resilient means for sealing a chromatography column positioned within said group.

2. A slurry compressor for use in a chromatographic column according to claim 1, wherein said resilient means for sealing comprises a resilient O-ring.

3. A slurry compressor for use in a chromatographic column according to claim 1, said groove further comprising means for receiving at least one backup spacer member.

4. A slurry compressor for use in a chromatographic column according to claim 1, wherein said walled structure comprises walls flaring slightly outwardly from said inner portion.

5. A slurry compressor for use in a chromatographic column according to claim 1, wherein said slurry compressor is formed of a polymer.

6. A slurry compressor for use in a chromatographic column according to claim 1, wherein said inner and outer portions of said slurry compressor are integrally connected.

7. A slurry compressor for use in a chromatographic column according to claim 1, wherein said resilient sealing means comprises a resilient O-ring and at least one backup spacer element positioned within said groove.

8. A slurry compressor for use in a chromatographic column according to claim 7, wherein said at least one backup spacer element is positioned between said O-ring and said generally planar surface.

9. A slurry compressor for use in a chromatographic column according to claim 7, wherein said backup spacer element comprises a split ring of glass loaded polymer.

10. A slurry compressor for use in a chromatographic column according to claim 7, wherein two backup spacer elements are positioned in said groove with said O-ring positioned between said spacer elements.

* * * * *

UNITED STATES PATENT AND TRADEMARK OFFICE
CERTIFICATE OF CORRECTION

PATENT NO. : 5,192,433
DATED : March 9, 1993
INVENTOR(S) : Yegyda Shalon

It is certified that error appears in the above-indentified patent and that said Letters Patent is hereby corrected as shown below:

At column 3, line 2, change "Absorbent, Bed" to ---Absorbent Bed---.
At column 5, line 64, change "means," to ---means---.
At column 8, line 64, "backup" should be ---back-up---.

Signed and Sealed this

Thirty-first Day of October 1995

Attest:

BRUCE LEHMAN

Attesting Officer        Commissioner of Patents and Trademarks